United States Patent [19]

Steiner et al.

[11] 4,362,727

[45] Dec. 7, 1982

[54] 5-SUBSTITUTED 9-CYANOMETHYLENE-DITHIENO[3,4-B:4,3-E]-AZEPINES AND THERAPEUTIC AGENTS WHICH CONTAIN THESE COMPOUNDS

[75] Inventors: Gerd Steiner, Kirchheim; Hans-Juergen Teschendorf, Ludwigshafen; Horst Kreiskott, Wachenheim; Hans P. Hofmann, Limburgerhof, all of Fed. Rep. of Germany

[73] Assignee: BASF Aktiengesellschaft, Fed. Rep. of Germany

[21] Appl. No.: 306,940

[22] Filed: Sep. 29, 1981

[51] Int. Cl.$^3$ .................. A61K 31/55; C07D 495/14
[52] U.S. Cl. .................. 424/248.51; 260/243.3; 260/244.4; 260/245.5; 260/245.6; 260/245.7; 260/330.3; 424/250; 424/267; 424/272; 424/273 R; 424/274; 424/275
[58] Field of Search .............. 260/243.3, 244.4, 245.5, 260/245.6, 245.7, 330.3; 424/248.51, 250, 267, 272, 273 R, 274, 275

[56] References Cited

U.S. PATENT DOCUMENTS 3,842,082  10/1974  Hunziker .................. 424/250 X

FOREIGN PATENT DOCUMENTS 2918778  11/1979  Fed. Rep. of Germany .
560220  3/1975  Switzerland .

OTHER PUBLICATIONS

Schmutz, Arzneim-Forsch, (Drug Research) 25, No. 5, (1975), pp. 712-720.

Primary Examiner—Richard Raymond
Attorney, Agent, or Firm—Keil & Witherspoon

[57] ABSTRACT

5-Substituted 9-cyanomethylene-dithieno[3,4-b:4',3'-e]-azepines, processes for their preparation, and therapeutic agents which contain these compounds and can be used as sedatives, hypnotic drugs, tranquillizers, neuroleptic drugs or anti-Parkinson drugs.

12 Claims, No Drawings

5-SUBSTITUTED 9-CYANOMETHYLENE-DITHIENO[3,4-b:4,3-e]-AZEPINES AND THERAPEUTIC AGENTS WHICH CONTAIN THESE COMPOUNDS

The present invention relates to 5-substituted 9-cyanomethylene-dithieno[3,4-b:4',3'-e]-azepines, processes for their preparation, and therapeutic agents which contain these compounds and can be used as sedatives, hypnotics, tranquillizers, neuroleptics or anti-Parkinson drugs.

It is known that tricyclic ring systems having a dibenzo structure on a central heterocyclic 7-membered ring, which may contain a basic side radical, for example N-methylpiperazinyl, can display neuroleptic effects. Such tricyclic ring systems are, for example, N-methylpiperazinyl derivatives of dibenzo[b,e][1,4]-diazepines (clozapine), dibenzo[b,f][1,4]-thiazepines (clotiapine), dibenzo[b,f][1,4]-oxazepines (loxapine) and morphanthridines (perlapine), as mentioned, for example, in the review by J. Schmutz in Arzneim.-Forsch. 25 (1975), 712–720.

German Patent Application No. P 2,918,778.8 proposes 6-substituted 11-alkylene-morphanthridines having valuable pharmacological properties. The present application relates to dithieno[3,4-b:4',3'-e] derivatives, which have a different pharmacological action profile.

We have found that 5-substituted 9-cyanomethylene-dithieno[3,4-b:4',3'-e]-azepines of the general formula I

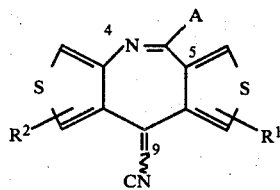

where $R^1$ and $R^2$ are hydrogen or halogen, especially chlorine, and A is $-NR^3R^4$, where $R^3$ and $R^4$, together with the nitrogen atom linking them, are a 5-membered to 7-membered saturated ring, which may contain nitrogen or oxygen as a further hetero-atom, an additional nitrogen present being unsubstituted or substituted by alkyl of 1 to 3 carbon atoms, hydroxyalkyl of 2 or 3 carbon atoms, alkoxyalkyl, where alkyl and alkoxy are of 1 to 3 carbon atoms, cycloalkyl or cycloalkylmethyl, where cycloalkyl is of 3 to 7 carbon atoms or alkynyl of 2 to 5 carbon atoms, and may additionally be substituted by oxygen in the form of an N-oxide, or A is $-NHR^5$, where $R^5$ is aminoalkyl of 2 to 7 carbon atoms, the amine nitrogen being unsubstituted or substituted by lower alkyl of 1 to 5 carbon atoms or being a constituent of a 5-membered to 7-membered saturated ring, which may contain nitrogen or oxygen as a further hetero-atom, a nitrogen present being substituted by lower alkyl of 1 to 3 carbon atoms or hydroxyalkyl of 2 or 3 carbon atoms, and their physiologically tolerated acid addition salts, have valuable pharmacological properties.

The radicals $R^1$ and $R^2$ are, in particular, hydrogen and chlorine, and in especially preferred compounds $R^1$ is hydrogen and $R^2$ is hydrogen or chlorine.

Examples of $-NR^3R^4$ radicals A are piperazinyl, homopiperazinyl, piperidinyl and morpholinyl radicals.

Particularly preferred $-NR^3R^4$ radicals are the 4-methylpiperazinyl, 4-methyl-4-oxy-piperazinyl, 4-ethyl-piperazinyl and N-methyl-homopiperazinyl radical.

In $-NHR^5$, $R^5$ is preferably the 2-dimethylamino-ethyl or 2-piperidin-1-yl-ethyl radical.

It is to be noted that the compounds according to the invention of the formula I exist as the cis/trans isomers Ia and b

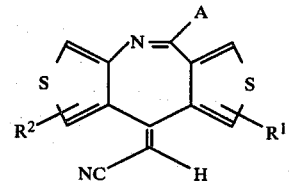

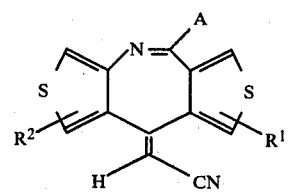

If desired, the cis/trans isomers can be separated, for example by fractional crystallization or by column chromatography.

On the basis of the above definitions, examples of compounds which are particularly preferred and effective are as follows: cis/trans-9-cyanomethylene-5-(4-methyl-piperazin-1-yl)-dithieno[3,4-b:4',3'-e]azepine, cis-9-cyanomethylene-5-(4-methyl-piperazin-1-yl)-dithieno[3,4-b:4',3'-e]azepine, trans-9-cyanomethylene-5-(4-methyl-piperazin-1-yl)-dithieno[3,4-b:4',3'-e]azepine, cis/trans-9-cyanomethylene-5-(4-methyl-4-oxy-piperazin-1-yl)-dithieno[3,4-b:4',3'-e]azepine, cis/trans-9-cyanomethylene-5-(4-ethyl-piperazin-1-yl)-dithieno[3,4-b:4',3'-e]azepine, cis/trans-9-cyanomethylene-5-(N'-methyl-homopiperazin-1-yl)-dithieno[3,4-b:4',3'-e]azepine, cis/trans-3-chloro-9-cyanomethylene-5-(4-methyl-piperazin-1-yl)-dithieno[3,4-b:4,',3'-e]azepine and cis/trans-9-cyanomethylene-5-(piperazin-1-yl)-dithieno[3,4-b:4',3'-e]azepine.

As the Examples show, separation into the cis- and trans-isomers can be carried out in an individual case without excessive expense.

The compounds according to the invention of the formula I are prepared by a process wherein a compound of the formula II

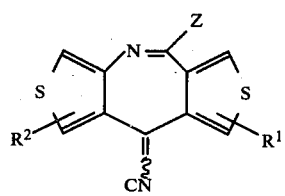

where $R^1$ and $R^2$ have the meanings and preferred meanings given in the case of formula I and Z is a nucleofugic leaving group, is reacted with a nucleophile AH, where A has the meanings given in the case of formula I, and the product is separated, if desired, into the pure cis- and trans-isomers, and/or the resulting compound is converted, if desired, into the N-oxide and/or into the acid addition salt of a physiological tolerated acid.

Nucleofugic leaving groups Z are halogen, in particular bromine and chlorine.

The reaction is advantageously carried out in the presence of an excess of the amine or alcohol AH used, which simultaneously serves as the solvent and, if appropriate, as an acid acceptor. Where relevant, an inert solvent can be used, such as a cyclic saturated ether, in particular tetrahydrofuran or dioxane, benzene or a benzene hydrocarbon, such as toluene, xylene, mesitylene or decahydronaphthalene, or an aprotic polar solvent, such as dimethylformamide. The reaction is as a rule carried out at from 80° to 150° C., preferably from 90° to 120° C., and generally has ended within from 3 to 10 hours. It may be advantageous to exclude atmospheric oxygen and to work under an inert gas, for example under nitrogen.

The nucleophile AH is advantageously used in from 2-fold to 20-fold or more molar excess.

A compound of the formula I is converted into the N-oxide in a conventional manner, advantageously using aqueous hydrogen peroxide (30% strength by weight) in ethanolic solution. Conversion to the acid addition salt of a physiologically tolerated acid is likewise effected in a conventional manner.

The starting compounds of the formula II are obtained by a process wherein a 9-cyanomethylene-dithieno[3,4-b:4',3'-e]-4,5-dihydro-azepin-5-one of the formula III

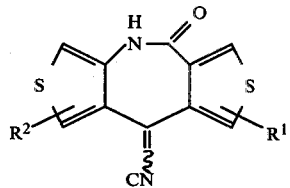

where $R^1$ and $R^2$ have the meanings given in the case of formula II, and an excess of a halogenating agent, in particular phosphorus oxychloride or phosphorus tribromide, are refluxed or heated at not more than 120° C., for 3-5 hours in a conventional manner, in the presence or absence of a solvent and in the presence or absence of a catalytic amount of N,N-dimethylaniline, and, after the excess phosphorus halide has been distilled off and the mixture has been worked up in an aqueous two-phase system, the resulting imino-chloride or -bromide is isolated by extraction with a chlorohydrocarbon, such as chloroform or methylene chloride.

The novel 9-cyanomethylene-dithieno[3,4-b:4',3'-e]-4,5-dihydro-azepin-5-ones of the formula III, where $R^1$ and $R^2$ have the meanings given in the case of formula I, are prepared by carbonyl-olefination, by reacting a dithieno[3,4-b:4',3'-e]-4,5-dihydro-azepine-5,9-dione of the formula IV

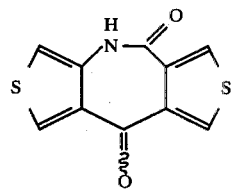

with a phosphonate of the formula Va

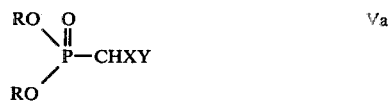

where R is alkyl of 1 to 3 carbon atoms and X and Y have the meanings given in the case of formula II, under the conditions of the wittig-Horner reaction, in an inert solvent, preferably dimethylformamide, and in the presence of one molar equivalent of a base, preferably a sodium alcoholate or sodium hydride or sodium amide, at from 20° to 80° C., or with a phosphonium salt of the formula Vb

where Ph is phenyl and X and Y have the meanings given in the case of formula Va, under the conditions of the classical Wittig reaction, in an aprotic organic solvent, in particular a saturated aliphatic or saturated cyclic ether, such as diethyl ether, tetrahydrofuran or dioxane, or, preferably, in dimethylformamide, and in the presence of one molar equivalent of a base, in particular an alkali metal alcoholate, preferably sodium methylate or ethylate, or sodium hydride, sodium amide or an organometallic compound, such as butyl-lithium, at from 20° to 100° C.

If required, the product is then converted into a compound of the formula III where $R^1$ and/or $R^2$ are chlorine or bromine, by halogenation with the equivalent amount of chlorine or bromine in an inert organic solvent, preferably a halohydrocarbon, such as carbon tetrachloride, chloroform or methylene chloride, at room temperature.

However, as described in the Examples, this halogenation can also advantageously be carried out, in the same manner, at the final stage. ie. on a compound of the formula I.

The novel dithieno[3,4-b:4',3'-e]4,5-dihydro-azepine-5,9-diones of the formula IV where $R^1$ and $R^2$ have the meanings given in the case of formula I are prepared by Schmidt ring enlargement of the 4,8-dihydro-benzo[1,2-c:4,5-c']-dithiophene-4,8-dione of the formula VI

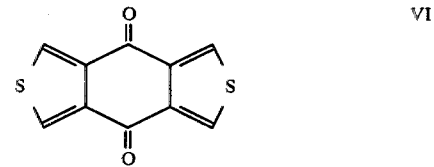

This reaction is carried out in a conventional manner, by taking up the 4,8-dihydro-benzo[1,2-c:4,5-c']dithiophene-4,8-dione in a mixture of a chlorohydrocarbon, preferably methylene chloride, and concentrated sulfuric acid (volume ratio from 1:2 to 1:1) and introducing 1 molar equivalent of sodium azide a little at a time at from 0° to 30° C., with thorough stirring.

The halo-derivatives of the dithieno[3,4-b:4',3'-e]-4,5-dihydro-azepine-5,9-dione of the formula IV can be prepared by direct halogenation in an organic solvent, preferably a halohydrocarbon, at from 0° to 80° C.

The starting material, 4,8-dihydro-benzo[1,2-c:4,5-c']-dithiophene-4,8-dione of the formula VI has been disclosed in the literature (D. W. H. MacDowell and J. C. Wisowaty, J. Org. Chem. 37 (1972), 1712).

In addition to the compounds mentioned in the Examples, the following compounds may also be mentioned: cis/trans-9-cyanomethylene-5-(4-cyclopropyl-piperazin-1-yl)-dithieno[3,4-b:4',3'-e]azepine, cis/trans-9-cyanomethylene-5-(4-cyclopropylmethyl-piperazin-1-yl)-dithieno[3,4-b:4',3'-e]azepine, cis/trans-9-cyanomethyl-5-(4-propin-2-yl-piperazin-1-yl)-dithieno[3,4-b:4',3'-e]azepine and cis/trans-3-bromo-9-cyanomethylene-5-(4-methylpiperazin-1-yl)-dithieno[3,4-b:4',3'-e]azepine.

The compounds of the formula I according to the invention are as a rule obtained in the form of yellowish or yellow crystals and can be purified by recrystallization from the usual organic solvents, preferably from a lower alcohol, such as ethanol, or by column chromatography.

If required, the compounds are separated into the individual cis- and trans-isomers by fractional crystallization in a chlorohydrocarbon, preferably methylene chloride, a lower monohydric alcohol, preferably methanol or ethanol, or a saturated cycloaliphatic hydrocarbon, preferably cyclohexane, or by column chromatography, in particular in methylene chloride and methanol in a volume ratio from 99:1 to 85:15.

The free 5-substituted 9-cyanomethylene-dithieno[3,4-b:4',3'-e]azepines of the formula I can be converted to addition salts of pharmacologically tolerated solids in a conventional manner, preferably by adding one equivalent of the appropriate acid to a solution of the compound. Examples of pharmaceutically tolerated acids are hydrochloric acid, maleic acid and methanesulfonic acid.

The compounds according to the invention exhibit valuable pharmacological properties. They can be used as sedatives, hypnotics, tranquillizers, neuroleptics or anti-Parkinson drugs. A compound according to the invention may possess a combination of several of the actions mentioned. In some cases, an individual pure isomer obtained by separation of isomers may preferentially display an action.

From the results of the pharmacological experiments carried out, the substances according to the invention are useful as sedatives/hypnotics, minor or major tranquillizers and anti-Parkinson drugs by virtue of their sedative/tranquillizing, muscle-relaxing and antimonaminergic action and their anticholinergic action on the central nervous system.

The following methods were used to analyze their action:

1. Sedative action

4–8 groups each of 3 female NMRI mice are given the compound orally. The orientation hypermotility induced by a new environment is determined photoelectrically, for a period of 30 minutes, starting 30 minutes after administration of the substances.

The ED50% is the dose which produces a 50% reduction in orientation hypermotility compared to placebo-treated control animals.

2. Muscle-relaxing action

The measurement is based on quantification of the tonic extension reflex in the gastrocnemius in rabbits (Teschendorf et al., Arch. Pharmacol. exp. path. 266 (1970), 462). The rabbit is kept in a special apparatus which allows it to flex its paw at the talocalcanean joint in a defined and reproducible manner. The flexing triggers off a tonic extension reflex in the calf muscles. The electrical activity of the muscle during the contraction is recorded, and the individual pulses are counted. The extension (lasting 5 seconds) is repeated at intervals of one minute. When a constant number of pulses (control value) has been reached, the test substance is administered intravenously. The numbers of pulses following the administration are compared with the initial values.

3. Antimethamphetamine action

Methamphetamine.HCl (2.5 mg/kg administered intravenously) regularly causes the following symptoms in rats: motor restlessness, searching and sniffing movements, fur standing on end, and tremor (Janssen et al., Arzneim.-Forsch./Drug Res. 13 (1963), 205; and Randrup et al., Psychopharmacologia 11 (1967), 300). The test substances are administered intraperitoneally 30 minutes before methamphetamine. The substance is considered to have an effect if no sniffing movements are observed for a period of 5 minutes after the injection of methamphetamine. The mean inhibition dose (ED50%) is determined, by means of probit analysis, as the dose which prevents the occurrence of the symptom in half the animals.

4. Anticholinergic action on the central nervous system

To test the anticholinergic action on the central nervous system, cholinergic stimulation is triggered off by pilocarpine. After rapid intravenous injection of pilocarpine.HCl (50 mg/kg) rats display alternating scratching movements of their rear paws; further symptoms triggered off in the central nervous system are jaw movements and tremors. Flow of saliva and chromodacryorrhea may be observed as signs of peripheral superexcitation (Kreiskott, Arch. exp. Path. Pharmak. 247 (1964), 317). The test substances are administered intraperitoneally 30 minutes before pilocarpine. The substance is considered to have an effect if no scratching is observed for a period of 2 minutes after the injection of pilocarpine. For this symptom, the mean inhibition dose (ED50%) is determined, by means of probit analysis by the method of Finney, as the dose of the test substance which suppresses the scratching in half the animals.

In these experiments (cf. Table 1), the compounds according to the invention were shown to have significant sedative/hypnotic effects which were about as powerful as those of the reference substance clozapine. They have a muscle-relaxing action which is somewhat weaker than that of clozapine, but as powerful as that of perlapine.

The antimonaminergic action (methamphetamine antagonism) may be evaluated as a parameter of the neuroleptic quality of a drug. The compounds according to the invention are as powerful as or significantly (up to 7 times) more powerful than the comparative compounds clozapine and perlapine.

The compounds also have an interesting anticholinergic action on the central nervous system, which in some cases is significantly more powerful than that of the reference substances. This type of action suggests that the novel substances can be used as anti-Parkinson drugs. On the other hand, because of this anticholinergic action on the central nervous system, no extrapyramidal motor disturbances are to be expected when the compounds are used as neuroleptics; such a connection is assumed for clozapine and should have a particularly advantageous effect in the case of the compounds according to the invention.

TABLE 1

| Example No. | Sedation ED 50%[+] | Sedation R.E.[++] | Muscle relaxation ED 50% | Muscle relaxation R.E. | Methamphetamine antagonism ED 50% | Methamphetamine antagonism R.E. | Anticholinergic action on the central nervous system ED 50% | Anticholinergic action on the central nervous system R.E. |
|---|---|---|---|---|---|---|---|---|
| 1a | 7.4 | 0.64 | 0.14 | 0.33 | 5.1 | 7.25 | 2.8 | 1.1 |
| 1b cis | 5.0 | 0.94 | 0.22 | 0.21 | 5.5 | 6.72 | 0.6 | 5.2 |
| 1b trans | >21.5 | <0.22 | >1.0 | <0.046 | 77 | 0.48 | 13 | 0.24 |
| 2 | 9.6 | 0.49 | 0.08 | 0.56 | — | — | — | — |
| 6 | 10.6 | 0.44 | 0.22 | 0.21 | 42 | 0.88 | — | — |
| Clozapine | 4.7 | 1.0 | 0.046 | 1.0 | 37 | 1.0 | 3.1 | 1.0 |
| Perlapine | 2.1 | 2.24 | 0.11 | 0.42 | 31 | 1.2 | 14.0 | 0.22 |

[+]mg/kg

[++]R.E. = relative effectiveness $\left( = \text{quotient } \dfrac{\text{ED 50\% comparative substance}}{\text{ED 50\% Example}} \right)$ Accordingly, the present invention also relates to a therapeutic agent which in addition to conventional carriers and diluents contains a compound of the formula I, or a pharmacogically tolerated acid addition salt thereof, as the active compound.

The therapeutic agents are prepared in a conventional manner by compounding an appropriate dose with the conventional carriers or diluents and the conventional industrial auxiliaries, in accordance with the desired route of administration. Suitable doses for man are from 10 to 100 mg.

The novel compounds may be employed in the conventional solid or liquid pharmaceutical forms, such as tablets, capsules, powders, granules, dragees or solutions. These are prepared in a conventional manner, and to do so the active compounds can be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. L. G. Goodman and A. Gilman, The Pharmacological Basis of Therapeutics). The formulations thus obtained normally contain from 0.001 to 99% by weight of the active compound.

The preferred formulations are those suitable for oral administration. Examples of these are tablets, film tablets, dragees, capsules, pills, powders, solutions, suspensions and depot forms. Parenteral formulations, such as injection solutions, may also be used. Suppositories are a further example of suitable formulations.

Appropriate tablets may be obtained, for example, by mixing the active compound with conventional auxiliaries, for example inert diluents, such as dextrose, sugar, sorbitol, mannitol, polyvinylpyrrolidone, calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets can also consist of a plurality of layers.

Correspondingly, dragees can be prepared by coating cores, prepared similarly to the tablets, with agents conventionally used in dragee coatings, for example collidone or shellac, gum arabic, talc, titanium dioxide or sugar. The dragee coating can also consist of a plurality of layers, and the auxiliaries mentioned above in connection with tablets may be used therein.

Solutions or suspensions containing the active compounds according to the invention may additionally contain flavor improvers, such as vanillin or orange extract. They may also contain suspending agents, such as sodium carboxymethylcellulose, or preservatives, such as p-hydroxybenzoates. Capsules containing the active compounds may be prepared, for example, by mixing the active compound with an inert carrier, such as lactose or sorbitol, and encapsulating the mixture in gelatin capsules. Suitable suppositories can be prepared, for example, by mixing the active compounds with appropriate carriers, such as neutral fats or polyethylene glycol or their derivatives.

The Examples which follow illustrate the present invention:

EXAMPLE 1

Cis- and trans-9-cyanomethylene-5-(4-methyl-piperazin-1-yl)-dithieno[3,4-b:4',3'-e]azepine (a) 140 ml of phosphorus oxychloride and 1.5 ml of N,N-dimethylaniline are added to 14.0 g (54 mmoles) of 9-cyanomethylene-4,5-dihydro-dithieno[3,4-b:4',3'-e]azepin-5-one (cis/trans-isomer mixture) and the mixture is refluxed under nitrogen for 1 hour. After all the excess phosphorus oxychloride and dimethylaniline have been distilled off under reduced pressure from an oil pump, the residue is partitioned between methylene chloride and water, the aqueous phase is extracted twice more with methylene chloride and the combined organic phases are washed thoroughly with dilute HCl and water. Drying and concentrating the organic phase gives 14.4 g (96%) of 5-chloro-9-cyanomethylene-dithieno[3,4-b:4',3'-e]azepine, which is sufficiently pure for the further reaction.

50 ml of N-methyl-piperazine are added to 14.4 g (52 mmoles) of 5-chloro-9-cyanomethylene-dithieno[3,4-b:4',3'-e]azepine and the mixture is stirred under nitrogen at 110° C. for 2 to 3 hours. After having been cooled, the dark homogeneous reaction mixture is poured onto ice-water and the yellowish crude 9-cyanomethylene-5-(4-methyl-piperazin-1-yl)-dithieno[3,4-b:4',3'-e]azepine is filtered off with suction. After the crude product has been dried in an oven under reduced pressure, it is recrystallized from ethanol, with the addition of active charcoal, or purified by column chromatography (silica gel, mobile phase: a 95/5 mixture of methylene chloride and methanol). 13.6 g (85%) of yellowish 9-cyanomethylene-5-(4-methyl-piperazin-1-yl)-dithieno[3,4-b:4',3'-e]azepine are obtained in the form of a cis/trans-isomer mixture of melting point 148°–151° C.

(b) To separate the cis/trans-isomers, the isomer mixture is subjected to fractional crystallization from ethanol. 6.5 g of yellow crystals which, according to the thin layer chromatogram (silica gel, mobile phase: an 85/15 mixture of toluene and methanol), chiefly consist of the non-polar cis-isomer a are isolated as the first fraction.

After the filtrate has been concentrated, the residue is digested in about 80 ml of boiling cyclohexane and the insoluble constituents are filtered off with suction, under the influence of heat. After having washed the product with a little cyclohexane, 2.1 g of yellow crystals, which, according to the thin layer chromatogram (silica gel, mobile phase: an 85/15 mixture of toluene and methanol) chiefly consists of the polar trans-isomer b, are obtained.

Subsequent crystallization of the enriched products from ethanol and cyclohexanone gives the cis- and trans-isomers in virtually pure forms. Melting point: cis-isomer: 200°–201° C., trans-isomer: 197°–198° C.

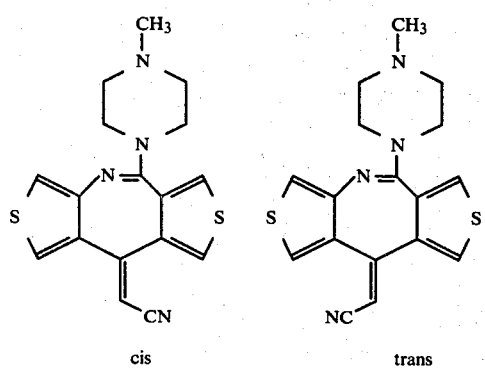

cis            trans

EXAMPLE 2

Cis/trans-3-chloro-9-cyanomethylene-5-(4-methylpiperazin-1-yl)-dithieno[3,4-b:4',3'-e]azepine 4.8 g (14 mmoles) of 9-cyanomethylene-5-(4-methyl-piperazin-1-yl)-dithieno[3,4-b:4',3'-e]azepine (cis/trans-isomer mixture) are dissolved in 160 ml of methylene chloride. 1.0 g (14 mmoles) of chlorine is then slowly passed in with thorough stirring (a finely crystalline solid precipitates). The mixture is stirred for a further 2 hours at room temperature and is then poured onto ice-water. After the mixture has been rendered basic with sodium hydroxide solution, the organic phase is separated off, the aqueous phase is extracted several times with methylene chloride and the combined organic phases are dried in a conventional manner. The crude product obtained on concentrating the organic phase is dissolved in a little boiling ethanol, active charcoal is added, the mixture is filtered hot and the solution is concentrated to a small volume. 45% of cis/trans-3-chloro-9-cyanomethylene-5-(4-methyl-piperazin-1-yl)-dithieno[3,4-b:4',3'-e]azepine having a melting point of 208°–211° C. crystalline in the cold.

EXAMPLE 3

Cis/trans-9-cyanomethylene-4,5-dihydro-dithieno[3,4-b:4',3'-e]azepin-5-one

The intermediate 9-cyanomethylene-4,5-dihydro-dithieno[3,4-b:4',3'-e]azepin-5-one is prepared by carbonylolefination of 4,5-dihydro-dithieno[3,4-b:4',3'-e]azepine-5,9-dione by the Wittig-Horner reaction or by the classical Wittig synthesis:

26.4 g (112 mmoles) of 4,5-dihydro-dithieno[3,4-b:4',3'-e]azepine-5,9-dione are dissolved in 300 ml of dimethylformamide, under the influence of heat, and the solution is stirred under nitrogen. 24.8 g (140 mmoles) of diethyl cyanomethyl phosphonate and 24.6 g (140 mmoles) of sodium ethylate (30%) dissolved in 30 ml of dimethylformamide are then simultaneously and slowly added dropwise (an intensification of color and increase in temperature indicate the start of the Wittig reaction). After the mixture has been stirred at room temperature for 12 hours, the reaction product is poured onto ice-water and the solid which precipitates is filtered off with suction. After the crude product has been washed thoroughly with water, it is dried and recrystallized from ethanol. Yield: 26.5 g (92%) of 9-cyanomethylene-4,5-dihydro-dithieno[3,4-b:4',3'-e]azepin-5-one as colorless crystals having a melting point of 253° C. (decomposition). Classical Wittig process: 1 molar equivalent of 30% strength sodium methylate solution is added dropwise, or 1 molar equivalent of sodium hydride is added, to triphenyl-cyanomethyl-phosphonium chloride in dimethylformamide and, finally, 1 molar equivalent of a solution of 4,5-dihydro-dithieno[3,4-b:4',3'-e]azepine-5,9-dione in dimethylformamide is added. The reaction mixture is then stirred at 50° to 80° C. for 5 to 8 hours and is subsequently poured onto ice-water and extracts several times with methylene chloride. After the organic phase has been dried and concentrated, the crude product is recrystallized from ethanol. Yield: 61% of colorless crystals having a decomposition point of 251°–253° C.

EXAMPLE 4

4,5-Dihydro-dithieno[3,4-b:4',3'-e]azepine-5,9-dione

The intermediate 4,5-dihydro-dithieno[3,4-b:4',3'-e]azepine-5-dione is prepared by Schmidt ring extension:

30.4 g (138 mmoles) of 4,8-dihydro-benzo[1,2-c:4,5-c']dithiophene-4,8-dione are suspended in 200 ml of methylene chloride; 280 ml of concentrated sulfuric acid are then added dropwise, with ice-cooling and stirring. A total of 13.0 g (200 mmoles) of sodium azide is then introduced a little at a time into the well stirred reaction mixture at 0° C. over a period of 2 hours. The mixture is then stirred at room temperature for 8 to 10 hours. The reaction mixture is poured carefully into 3 l of ice-water, with thorough stirring, and the solid which precipitates after a short time is filtered off with suction. The crude product is washed with a large amount of water until it gives a neutral reaction, and is dried at 50° C. under reduced pressure.

28.0 g (86%) of a light solid which has a melting point of 267°–270° C. and is sufficiently pure for the further reaction are isolated.

EXAMPLE 5

Cis/trans-9-cyanomethylene-5-(4-methyl-4-oxy-piperazin-1-yl)-dithieno[3,4-b:4',3'-e]azepine.2H$_2$O 3.5 g (11 mmoles) of cis/trans-9-cyanomethylene-5-(4-methyl-piperazin-1-yl)-dithieno[3,4-b:4',3'-e]azepine are dissolved in 100 ml of hot ethanol, and 1.5 ml of 30% strength hydrogen peroxide are added. After the mixture has been refluxed for 5 hours, the excess hydrogen peroxide is decomposed by introducing a small platinum foil into the reaction mixture and refluxing the mixture for 2 hours. When the reaction mixture has been filtered, it is concentrated, and the resulting N-oxide is purified by column chromatography (silica gel, mobile phase: a 95/5 mixture of methylene chloride and methanol). 1.8 g (50%) of yellow crystals having a melting point of 137°–140° C. are isolated.

EXAMPLE 6

Cis/trans-9-cyanomethylene-5-(4-ethyl-piperazin-1-yl)dithieno[3,4-b:4′,3′-e]azepine This compound is synthesized by a method similar to that in Example 1a, using N-ethylpiperazine. After column chromatography (silica gel, mobile phase: a 95/5 mixture of methylene chloride and methanol), yellow crystals having a melting point of 118°–121° C. are obtained.

EXAMPLE 7

Cis/trans-9-cyanomethylene-5-(N′-methyl-homopiperazin-1-yl)-dithieno[3,4-b:4′,3′-e]azepine.$H_2O$ This compound is synthesized by a method similar to that in Example 1a, using N-methyl-homopiperazine. Purification by column chromatography (silica gel; a 95/5 mixture of methylene chloride and methanol) gives yellow crystals having a melting point of 124°–126° C.

EXAMPLE 8

Cis/trans-9-cyanomethylene-5-[2-(piperidin-1-yl)-ethylamino]-dithieno[3,4-b:4′,3′-e]azepine.½$H_2O$ This compound is synthesized by a method similar to that in Example 1a, using 2-piperidin-1-yl-ethylamine. Purification by column chromatography (silica gel; a 95/5 mixture of methylene chloride and methanol) gives yellow crystals having a melting point of 112°–114° C.

EXAMPLE 9

Cis/trans-9-cyanomethylene-5-piperazin-1-yl-dithieno[3,4-b:4′,3′-e]azepine

This compound is synthesized by a method similar to that in Example 1a, using 5 molar equivalents of piperazine and increasing the aminolysis temperature to 140° C. After the reaction melt has cooled, it is taken up in methylene chloride, the organic phase is thoroughly washed three times with water and the crude product is purified by column chromatography (silica gel; a 95/5 mixture of methylene chloride and methanol) to give yellow crystals having a melting point of 94°–96° C.

Examples of pharmaceutical formulations:

| Examples of tablets | |
|---|---|
| 1. An active compound of formula I | 10 mg |
| Lactose | 200 mg |
| Methylcellulose | 15 mg |
| Corn starch | 50 mg |
| Talc | 11 mg |
| Magnesium stearate | 4 mg |
| 2. An active compound of formula I | 20 mg |
| Lactose | 178 mg |
| Avicel | 80 mg |
| Polywax 6000 | 20 mg |
| Magnesium stearate | 2 mg |
| 3. An active compound of formula I | 50 mg |
| Polyvinylpyrrolidone (mean molecular weight 25,000) | 170 mg |
| Polyethylene glycol (mean molecular weight 4,000) | 14 mg |

| -continued | |
|---|---|
| Examples of tablets | |
| Hydroxypropylmethylcellulose | 40 mg |
| Talc | 4 mg |
| Magnesium stearate | 2 mg |

The active compound is moistened with a 10% strength aqueous solution of polyvinylpyrrolidone and forced through a sieve of 1.0 mm mesh size, and the granules are dried at 50° C. They are then mixed with polyethylene glycol (mean molecular weight 4,000), hydroxypropylmethylcellulose, talc and magnesium stearate, and the mixture is pressed to give tablets weighing 280 mg.

| 4. Examples of dragees | |
|---|---|
| An active compound of formula I | 60 mg |
| Lactose | 90 mg |
| Corn starch | 60 mg |
| Polyvinylpyrrolidone | 6 mg |
| Magnesium stearate | 1 mg |

The active substance, lactose and corn starch are mixed, moistened with an 8% strength aqueous solution of the polyvinylpyrrolidone, and granulated by passing through a 1.5 mm sieve. The granules are dried at 50° C. and again forced through a 1.0 mm sieve. The material thus obtained is mixed with magnesium stearate and the mixture is pressed to form dragee cores. These are coated in a conventional manner with a shell consisting essentially of sugar and talc.

| 5. Capsule formulation | |
|---|---|
| An active compound of formula I | 5 mg |
| Magnesium stearate | 2.0 mg |
| Lactose | 19.3 mg |
| 6. Injection solution | |
| An active compound of formula I | 10 mg |
| Sodium chloride | 9 mg |
| Distilled water, to make up to 1.0 ml | |

We claim:

1. A 5-substituted 9-cyanomethylene-dithieno[3,4-b:4′,3′-e]azepine of the formula I

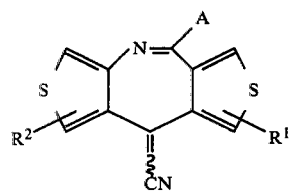

where $R^1$ and $R^2$ are hydrogen or halogen, and A is —$NR^3R^4$, where $R^3$ and $R^4$, together with the nitrogen atom linking them, are a 5-membered to 7-membered saturated ring, which may contain nitrogen or oxygen as a further hetero-atom, an additional nitrogen present being unsubstituted or substituted by alkyl of 1 to 3 carbon atoms, hydroxyalkyl of 2 or 3 carbon atoms, alkoxyalkyl, where alkyl and alkoxy are of 1 to 3 carbon atoms, cycloalkyl or cycloalkylmethyl, where cycloalkyl is of 3 to 7 carbon atoms or alkynyl of 2 to 5 carbon atoms, and may additionally be substituted by oxygen in the form of an N-oxide, or A is —$NHR^5$, where $R^5$ is aminoalkyl of 2 to 7 carbon atoms, the amine nitrogen being unsubstituted or substituted by lower alkyl of 1 to 5 carbon atoms or being a constituent of a 5-membered to 7-membered saturated ring, which may contain nitrogen or oxygen as a further hetero-atom, a nitrogen present being substituted by lower alkyl of 1 to 3 carbon atoms or hydroxyalkyl of 2 or 3 carbon atoms, and its physiologically tolerated acid addition salts.

2. A compound of the formula I as defined in claim 1 wherein $R^1$ and $R^2$ are hydrogen or chlorine or bromine.

3. A compound of the formula I as claimed in claim 1, where $R^1$ and $R^2$ are hydrogen, chlorine or bromine and A is piperidine, piperazine or homopiperazine, in which any ring nitrogen atom present is substituted by H, methyl, ethyl, β-hydroxyethyl, cyclopropyl or propynyl and may be in the form of the N-oxide.

4. A compound of the formula I as claimed in claim 1, where $R^1$ is hydrogen, $R^2$ is hydrogen or chlorine and A is 4-methyl-piperazin-1-yl, 4-ethyl-piperazin-1-yl, 4-methyl-4-oxy-piperazin-1-yl or N'-methyl-homopiperazin-1-yl.

5. Cis/trans-9-cyanomethylene-5-(4-methyl-piperazin-1-yl)-dithieno[3,4-b:4',3'-e]azepine.

6. Cis-9-cyanomethylene-5-(4-methyl-piperazin-1-yl)dithieno[3,4-b:4',3'-e]azepine.

7. Trans-9-cyanomethylene-5-(4-methyl-piperazin-1-yl)-dithieno[3,4-b:4',3'-e]azepine.

8. Cis/trans-9-cyanomethylene-5-(4-methyl-oxy-piperazin-1-yl)-dithieno[3,4-b:4',3'-e]azepine.

9. Cis/trans-9-cyanomethylene-3-chloro-5-(4-methyl-piperazin-1-yl)-dithieno[3,4-b:4',3'-e]azepine.

10. Cis/trans-9-cyanomethylene-5-(4-ethyl-piperazin-1-yl)-dithieno[3,4-b:4',3'-e]azepine.

11. Cis/trans-9-cyanomethylene-5-(N'-methyl-homopiperazin-1-yl)-dithieno[3,4-b:4',3'-e]azepine.

12. A therapeutic composition contains, in addition to conventional carriers and diluents, a compound of the formula I as claimed in claim 1, or a pharmacologically tolerated acid addition salt thereof, as the active compound.

* * * * *